United States Patent [19]
Leader et al.

[11] Patent Number: 5,421,981
[45] Date of Patent: Jun. 6, 1995

[54] ELECTROCHEMICAL SENSOR STORAGE DEVICE

[75] Inventors: Matthew J. Leader, Laguna Niguel, Calif.; Kee V. Sin, White Bear Lake, Minn.

[73] Assignee: PPG Industries, Inc., Pittsburgh, Pa.

[21] Appl. No.: 147,411

[22] Filed: Nov. 5, 1993

Related U.S. Application Data

[63] Continuation of Ser. No. 4,493, Jan. 14, 1993, abandoned, which is a continuation of Ser. No. 721,027, Jun. 26, 1991, abandoned.

[51] Int. Cl.⁶ .............................................. G01N 27/26
[52] U.S. Cl. .................................... 204/409; 204/403; 128/635
[58] Field of Search ............... 204/409, 153.17, 153.1, 204/402, 415, 400, 403, 422; 128/635

[56] References Cited

U.S. PATENT DOCUMENTS

| | | | |
|---|---|---|---|
| 3,000,805 | 9/1961 | Carritt et al. | 204/195 |
| 3,049,118 | 8/1962 | Arthur et al. | 128/4 |
| 3,088,905 | 5/1963 | Glover | 204/195 |
| 3,497,442 | 2/1970 | Vincent | 204/195 |
| 3,681,255 | 8/1972 | Wilfore | 262/408 |
| 3,912,614 | 10/1975 | Spracklen et al. | 204/195 B |
| 4,150,744 | 4/1979 | Fennimore | 206/205 |
| 4,339,317 | 7/1982 | Meiattini et al. | 204/195 B |
| 4,449,632 | 5/1984 | Marusiak, Jr. | 206/540 |
| 4,548,605 | 10/1985 | Iwamoto et al. | 604/410 |
| 4,615,340 | 10/1986 | Cronenberg et al. | 128/635 |
| 4,654,127 | 3/1987 | Baker et al. | 204/1 T |
| 4,664,256 | 5/1987 | Halskoy | 206/213 |
| 4,734,184 | 3/1988 | Burleigh et al. | 204/415 |
| 4,818,361 | 4/1989 | Burgess et al. | 204/406 |
| 4,863,016 | 9/1989 | Fong et al. | 206/210 |
| 4,929,426 | 5/1990 | Bodai et al. | 422/63 |
| 5,046,496 | 9/1991 | Betts et al. | 204/403 |
| 5,096,669 | 3/1992 | Lauks et al. | 422/62 |
| 5,098,545 | 3/1992 | Patko | 204/403 |

FOREIGN PATENT DOCUMENTS

| | | |
|---|---|---|
| 0015075 | 9/1980 | European Pat. Off. |
| 0027385 | 4/1981 | European Pat. Off. |
| 0351516 | 7/1988 | European Pat. Off. |

OTHER PUBLICATIONS

Declaration of Dr. Ronald E. Betts, dated Sep. 1994.
Declaration of Matthew J. Leader, dated Sep. 1994.
"Medical and Biological Engineering Computing", vol. 16, 1978, pp. 599–600 no month available.
"Quality Control in Blood pH and Gas Analysis by Use of a Tonometered Bicarbonate Solution and Duplicate Blood Analysis" *Journal of Clinical Chemistry*, vol. 27, No. 10, 1981, pp. 1761–1763 no month available (Abstract).
Affidavit of Walter Sembrowich including at Exhibit B photostatic copies of two items no month available.
Information Brochure entitled "Pick A Card" by Johnson & Johnson Professional Diagnostics Inc. (1988) no month available.
Information Brochure entitled "World Wide" by Johnson & Johnson Professional Diagnostics Inc. vol. 22, No. 5, Dec. 1987), pp. 1–19.
"Sentech Part I: First Blood" of *Corporate Report Minnesota* by James Thornton, Oct. 1985.
Arden Medical Systems, Inc. Prospectus, 1986 no month available.

*Primary Examiner*—John Niebling
*Assistant Examiner*—Bruce F. Bell
*Attorney, Agent, or Firm*—Kenneth J. Stachel

[57] ABSTRACT

A sensor apparatus is provided that is the sensor with or without accompanying sample collector means and calibration means in a hermetically sealed layer that contains at least one preconditioning fluid. The preconditioning fluid is an activating fluid when the sensor is in an unsealed housing and can be either or both the activating fluid or a controlled-content fluid when the sensor is in a sealed housing. The sealed housing is one that has the preconditioning fluid sealed in fluid contact with the one or more sensors on a sensor element. The sensor element also has an electrical circuit means in electrical contact with the one or more sensor on a nonconducting substrate. When both preconditioning fluids are present the activating fluid is in fluid contact with the one or more sensors in the sealed housing and the known-content fluid is present in the atmosphere in the hermetically sealed layer outside the sealed housing. The sealed layer is impervious to gas and moisture and is a diffusion-tight boundary or barrier.

31 Claims, 3 Drawing Sheets

5,421,981

ELECTROCHEMICAL SENSOR STORAGE DEVICE

This application is a continuation of application Ser. No. 08/004,493, filed Jan. 14, 1993, now abandoned, which is a continuation of application Ser. No. 07/721,027, filed Jun. 26, 1991, now abandoned.

The present invention is directed to a device or apparatus for preconditioned analyte detecting sensors that can be used in a portable manner or are ready for use in detecting analyte.

BACKGROUND OF THE INVENTION

Current technology utilizes many types of sensors for detecting components, analytes, in numerous types of fluids. For example, some of these range from oxygen sensors for detecting oxygen in air for control of the air and fuel ratio for combustion in internal combustion engines to multiple phase sequential analyzers for qualitative and/or quantitative measurement of constituents or analytes of blood. For instance, the measurement of blood gases, usually a measure of the partial pressures of oxygen and carbon dioxide, along with the pH from a sample of arterial blood gives the state of the acid base balance or the effectiveness of both the respiratory and cardiovascular systems of the human or vertebrate body. These various types of sensors can be prepared by various techniques including layered circuit or integrated circuit technologies, as for example, thick film, thin film, plating, pressurized laminating and photolithographic etching, and other like silk screening processes.

Many of these sensors require some form of preparation before they are ready for use in measuring analytes in samples. If the thick film sensors have an electrolyte that is substantially aqueous, the membrane of the sensor would probably need hydrating prior to use. This situation would arise when the analysis equipment is started or when a sensor in the equipment is changed. The hydration process would be time consuming for performance on the equipment and would probably be performed in a separate operation prior to installation in the equipment. Also the sensors are usually calibrated prior to measuring analyte in samples by passing reference samples with known values of analytes by the sensors. If improper results are obtained the integrity of the sensor may be a question. The integrity of a sensor may even be a question for a sensor that is newly installed in the equipment so that diagnostic testing might be in order upon such an installation.

In addition to the use of sensors in stationary analysis equipment, portable analysis equipment is being developed which place additional demands on the sensors. For instance, technology has developed portable analysis devices that can shorten or overcome transporting the samples to stationary equipment which can be burdensome and in some instances deleterious to the accuracy of the results of the measurements. For measuring constituents of blood, the blood sample is drawn from the patient and usually, as in the case of blood gases, transported to a central location for testing. There are many reports in the literature that suggest that the values obtained in the measurement of blood gases depend on the type of measuring equipment and the technique for sample collection.

To overcome this problem technology has been developed to eliminate this transportation operation as much as possible so that a patient's blood gases could be measured at the bedside in a manner similar to measuring a patient's temperature U.S. Pat. Nos. 3,000,805 and 3,497,442 show two such devices. The former has sensors located on a syringe plunger and the latter has sensors placed on the syringe well to conduct the measurements. In the allowed United States patent application Ser. No. 07/343,234, Applicants assignee describes and claims a portable blood gas sensor which includes sensors fabricated from a conventional silk screening process where the sensors are screened on to a ceramic substance. Typically these sensors have electrodes used in conjunction with an electrolyte and with an analyte permeable membrane that covers the sensor. These portable sensors still should be calibrated like the stationary equipment so one or more of the reference fluids can be used with these portable devices.

It is an object of the present invention to provide a sensor in a ready-to-use state for stationary analysis equipment and especially in a ready-to-use state for a portable analysis device to make such a device more user friendly and actually more portable,

SUMMARY OF THE INVENTION

The foregoing objects and others gleaned from the following disclosure are accomplished by the sensor assembly apparatus of the present invention.

The sensor apparatus of the present invention has a sensor assembly having a sensor element and a housing where the assembly is surrounded by and hermetically sealed in a fluid impermeable diffusion-tight envelope. Also, in between the sensor assembly and the envelope, a preconditioning fluid is present in contact with the sensor assembly. The sensor element has the one or more sensors disposed in conjunction with a nonconducting substrate that also has an electrical circuit means communicating with the one or more sensors for at least a transmission of signals from the sensors. The housing provides for fluid contact of at least a sample fluid with the one or more sensors of the sensor element. The preconditioning fluid can be an activating fluid to maintain the sensors in an active state and/or an controlled-content fluid having a known amount of one or more analytes that are measured by the one or more sensors. When both the activating fluid and the controlled-content fluids are present, the activating fluid is in sealed contact with the one or more sensors and the controlled-content fluid is in contact with the sealed sensor assembly to equilibrate with the one or more sensors to maintain the sensor in a precalibrated state. The sealed contact is provided by the housing where some portion of the housing is gas permeable over a period of time. This allows an equilibration of gas between the controlled-content fluid and the activating fluid in fluid contact with the one or more sensors. In addition to the presence of the sensor assembly in the hermetically-sealed envelope, there can also be present a sample delivery device and/or a calibrant delivery device.

DETAILED DESCRIPTION AND PREFERRED EMBODIMENT OF THE INVENTION

Figure 1:
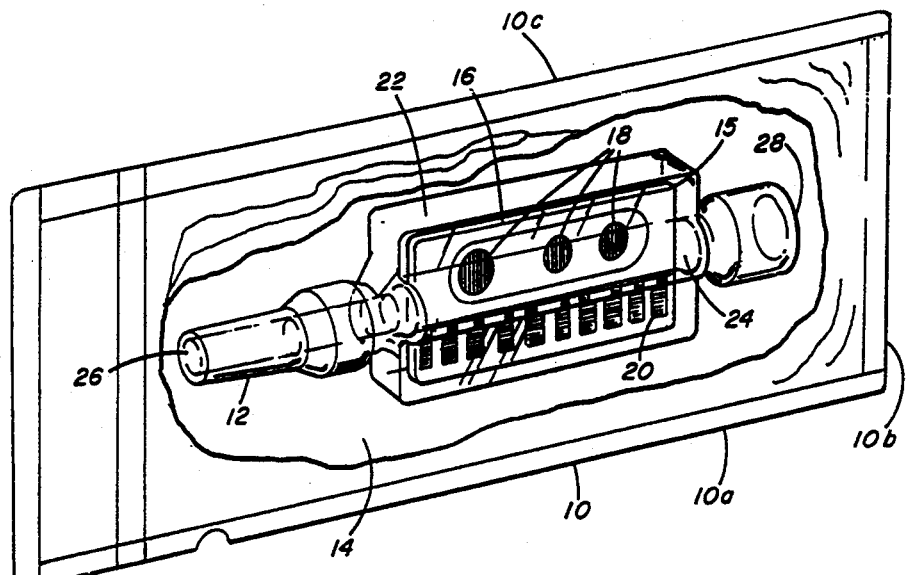
FIG. 1 is a front view of the apparatus of the present invention with a cut-away sectional view to display the interior of the envelope and the contents of the interior including the sensor.

In the following description and in the claims the below-listed terms having the following indicated meanings.

In this description and in the accompanying claims, the term "equilibrating" is used in its art-recognized sense to mean that the gas and the buffer solution are maintained in contact with each other until such time as a state of equilibrium has been reached between the analyte in the controlled-content fluid and the analyte in the activating fluid.

The term "active state" for the sensor refers to the condition of the sensor that it is ready to detect analyte although calibration may be needed with conventional reference fluids.

"Preconditioned state" of the sensor refers to providing a sensor that is either in its active state and/or is in a diagnostic state, and/or is in a pseudo- or precalibration state and/or is in a calibrated state. The diagnostic state is that where the sensitivity of the sensor can be tested initially on first using the sensor with a display device not shown in the drawings. With this diagnostic information the sensor can be tested for its ability to function prior to using it in analysis equipment. The pseudo or precalibration state is when the output from a calibrant or reference sample with a predetermined amount of analyte is compared with an output reading on a subsequent calibration or reference sample and a particular range of the change in values is expected for good operability of the sensor. Calibrated state is when the sensor initially gives an output reading on display equipment of some value or values for a calibrant or reference sample with a predetermined amount of one or more analytes.

Figure 2:
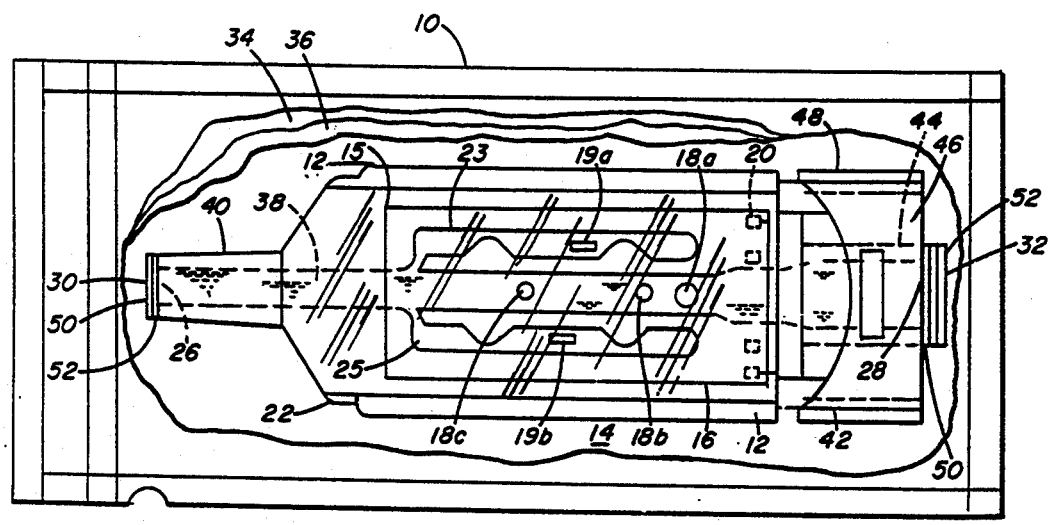
FIG. 2 is a front view of the apparatus of the present invention with a cut-away sectional view to display the interior of the envelope and the contents thereof including the sensor in a preferred arrangement.
Figure 3:
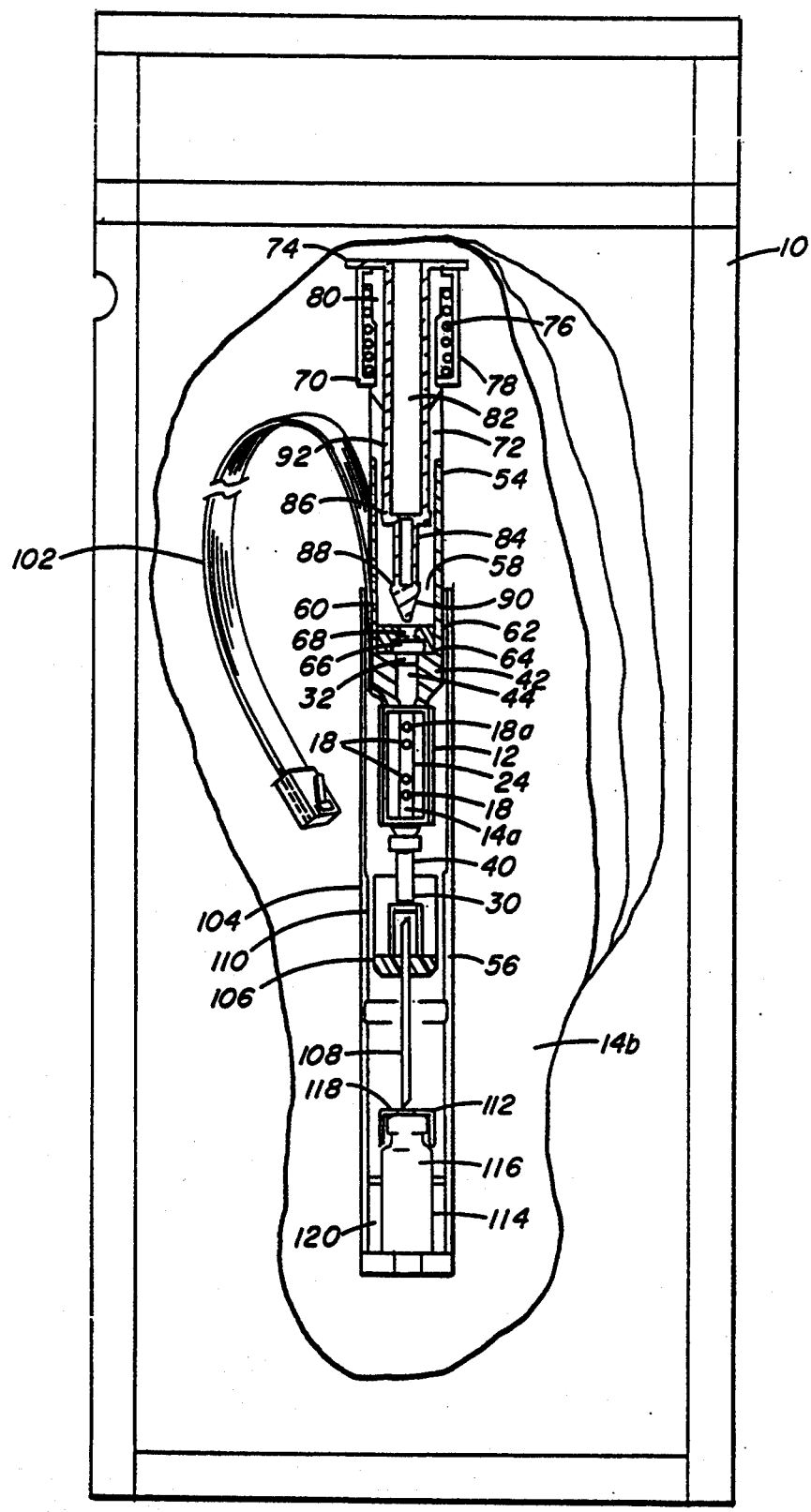
FIG. 3 is a front view of the apparatus of the present invention with a cut-away section to display the interior of the envelope and the contents thereof including the sensor and syringe member and calibrant delivery member.

In FIGS. 1-3, similar numerals are used throughout the drawings to denote the same feature in each of the drawings.

In FIG. 1 the hermetically sealable envelope that is gas impermeable and diffusion tight can be any single layer or multiple layer laminate type material that has these characteristics. Suitable multilayer material includes metal foil polymer laminate material that can be heat-sealed or RF (radio frequency) sealed to form a bag. The laminate material ordinarily has the interior layer of polymeric material and outside this layer a metal foil layer. The thickness of the inner polymeric or plastic layer is generally in the range of about 20 to around 80 microns. A typical laminate can have two or more layers but preferably has an additional outer polymeric layer to facilitate abrasion resistance or printing on top of the metal foil layer. A nonexclusive example of the metal foil is aluminum.

The three layer laminate suitable for the envelope of the present invention as shown in FIGS. 1, 2 and 3 as 10 can have from the exterior surface to the interior layer the following:

1) nylon, polyester polyethylene or polypropylene, for example, 10 to 70 grams per meter$^2$ thickness for abrasion resistance,
2) aluminum foil, for example, 5 to 40 grams per meter$^2$ thickness, and
3) an inner heat sealable polymeric layer such as polyethylene, polypropylene, polyvinylidene chloride or nylon, i.e., of 5 to 25 grams per meter$^2$ thickness. A nylon-foil-polypropylene laminate of, i.e., 17 grams per meter$^2$ nylon, 32 grams per meter$^2$; aluminum, 45 grams per meter$^2$; polypropylene available under the trade name Sterilite NFP is suitable.

Another suitable example is a laminate having as an outer layer polyvinyl alcohol in an inner layer of a heat sealable polymeric material such as polyethylene, polypropylene, high-density polyethylene, polyester, a laminate consisting of non-stretch polypropylene and biaxially stretched polypropylene and an inner layer of non-stretch polypropylene and nylon as an intermediate layer and biaxially stretched polypropylene as an outer layer. Any of these heat-sealable polymeric films can be used as the inner layer with the polyvinyl alcohol. The hydroxyl groups of the polyvinyl alcohol are bonded with each other through hydrogen bonding providing polyvinyl alcohol with an extremely high impermeability (barrier property) to oxygen gas. The inner layer of the heat sealable polymeric film improves the heat sealability of the polyvinyl alcohol laminate. In addition, to retard deleterious effects of moisture or water in the environment on the polyvinyl alcohol layer a third polymeric layer is the exterior layer over the polyvinyl alcohol layer. Suitable examples for this layer include biaxially stretched polypropylene, polyester, biaxially stretched nylon and polyvinylidene chloride film. A suitable laminate layer of this type is available commercially under the trade designation EVAR from Kuraray, Ltd.

A still further example of a suitable example is a poly-foil-polylaminate which is a three-layer composite having an aluminum foil intermediate layer and an inner and outer layer of polypropylene. In the metal foil laminate layer, the thickness of the aluminum foil is generally in the range of at least 20 microns to about 30 microns. The inner polymeric layer can also be selected from low permeable thermoplast available from ICI Chemicals, polyvinylidene chloride available under the trade designation SARAN, polyacrylonitrile-copolyme available under the trade designation PANC and BARAX 210; polyethylene terephthalate available under the trade designation MYLAR, polyvinylfluoride available under the trade designation PVF and polyamide-6 available under the trade designation NYLON-6 and polyvinyl chloride. The PANC is available from Lonzag, 4002 Basel and is described as a copolymer of a high proportion of acrylonitrile about 72 percent by weight and a low portion of other monomers, that is thermoelastically workable up to a temperature of about 150° C.

A bag of the layer or an envelope is formed by any method known to those skilled in the art such as heat sealing or RF sealing. The size of the bag formed by the layer 10 will vary depending on the contents of the bag and can range from a size of about 4×7 cm to 6×10 cm to larger dimensions when additional components are included in the bag in addition to the sensor assembly; for instance, from 6 to 15 cm wide to 10×20 cm long and can include a tear strip or tearing notch or line of weakness or the like expedient to facilitate opening. The seals can be placed along each end of the layer folded on itself or for two layers facing each other with their heat sealable polymeric layers, the inner layer of each edge can be sealed. Heat seals for the material folded on itself would be along two edges and one folded side like 10a, 10b and 10c of FIG. 1. For two pieces of material facing each other, three heat seals would be made—one at each end like 10a through 10c. Typically, the heat seals 10a through 10c can be 9 to 10 mm wide. The heat seals are applied to the layer to allow for one open end of the bag. After the components are added to the bag the opening is heat sealed in the same manner as the other sides.

The sensor assembly 12 has the sensor element 15 with a nonconducting substrate 16 with one or more sensors like sensor 18 and an electrical circuit means 20 electrically connected to at least one sensor to at least transmit or convey signals from the sensor. Generally, the nonconducting substrate 16 can be a glass or ceramic including sheet or chip or nonconducting substrate like nonconducting polymers or commercially available frit that can be used as the substantially smooth flat surface for the nonconducting substrate. Nonexclusive examples include borosilicate glass as is known to those skilled in the art for producing thick film or layered circuits. A nonexclusive but preferred example of which includes a ceramic base having around 96% Al2O3 such as that available commercially from Coors Ceramic Company, Grand Junction, Colo. Generally, the electrical circuit means 20 is any electrical circuit means known by those skilled in the art. For example, means 20 can communicate with the one or more sensors by layered or patterned paths (not shown in the drawings) to the sensors on either side of the nonconducting substrate. If the electric circuit means is on the other side of the substrate from the one or more sensors the paths extend through the substrate in appropriately drilled holes. Both the sensor 18 and the electrical circuit means 20 can be prepared from any number of well known layered circuit or integrated circuit technologies, as for example, thick film, thin film, plating, pressurized laminating and photolithographic etching, and the like, however, the thick film technique is preferred. A suitable sensor assembly is that described in the allowed U.S. patent application Ser. No. 07/343,234, filed on Apr. 26, 1989, U.S. Pat. No. 5,046,496, and titled, "Sensor Assembly for Measuring Analytes in Fluids, which is commonly assigned, and which is incorporated herein by reference.

The at least one sensor 18 can be a potentiometric or amperometric sensor, in that the former has one electrode and the latter has two, both an anode and a cathode. In the situation where the sensor 18 is potentiometric, an additional electrode is usually present as a reference electrode. Any reference electrode known to those skilled in the art can be used. The potentiometric or amperometric sensor preferably has a water vapor permeable polymeric membrane and the sensor preferably has an aqueous-based electrolyte with suitable ionized chemical species. Suitable examples of such membranes that are present in electrochemical sensors for use in determination of blood gases are described in U.S. Pat. Nos. 3,088,905 and 3,912,614 and European patent specifications 0015075 and 0027385 and the article in the journal entitled "Medical and Biological Engineering Computing", 1978, Vol. 16, pages 599–600. The publications describe blood gas detectors requiring the presence of membranes and a number of useful or potentially useful membrane materials. A suitable example of a water vapor permeable polymeric membrane is polyvinylchloride and modified polyvinylchloride.

In FIG. 1, the preconditioning fluid 14 is an activating fluid to maintain the sensor or sensors in an active state. For example, a sensor may have a water vapor permeable polymeric membrane like a hydratable polymeric membrane with some portion of its electrolyte that is aqueous. In this situation the sensor needs to be maintained in a hydrating fluid to be active. Some sensors with hydratable membranes may be stored dry but they need the hydration of their membranes for the existence of an active state. When the sensor assembly 12 has at least one such sensor at 18 that requires hydration for activity, the preconditioning fluid 14 is the activating fluid. Preconditioning fluid 14 is in fluid contact with the sensor by the sealed presence of the fluid within the bag formed by layer 10. In this manner the preconditioning fluid is between the gas impervious, diffusion tight layer and the sensor by its presence within the bag in fluid contact with the sensor. Nonexclusive examples of such an activating fluid used as the atmosphere in the layer 10 are: moist air or air with a relative humidity greater than around 30 percent, or super-saturated moist air, or any similar moisture-containing or moisture-ladened inert gas.

FIG. 1 shows housing 22 as part of the sensor assembly. This housing can be any container having any geometric shape for the sensor 18, non-conducting substrate 16, and electrical circuit 20 and that allows the sensor to interface with a sample that is to be tested. The extent of the housing can vary in relation to the assembly components that are in the housing. The housing can be a cover for or chamber over the one or more sensors for the housing 22 to provide fluid contact where the sensor element 15 forms the back of the assembly 12. The housing can be made of any fairly rigid moldable material such as rigid thermoplastic polymers although thermosetting polymers can also be used. Suitable nonexclusive examples include: methyl methacrylate styrene butadiene terpolymer and rigid plastics such as polyesters like polyethyleneterephthlate or polycarbonate or blends or alloys thereof. Another form of housing 22 can be as an enclosure for sensor element 15 and having one or more openings for fluid contact with the one or more sensors.

The housing 22 contains a channel 24 that interfaces with the sensor 18 in such a manner that a fluid sample can be placed in fluid contact with the sensor 18. The channel can have any shape or configuration to accomplish this interface. Generally, the channel has an inlet 26 to receive the sample and outlet 28 to remove the sample from the vicinity of the sensor 18. Shapes and configurations of the inlet and outlet other than shown in FIG. 1 and known to those skilled in the art can be used that accomplish this function. In addition to the fluid 14 occupying the environs between the sealed bag and the housing 22, the fluid can also occupy the channel 24 which may be sealed in a similar manner as discussed below for FIG. 2 or may remain unsealed.

FIG. 2 shows an embodiment where the preconditioning fluid 14 is an activating fluid or controlled-content fluid or both fluids by the presence of two separate fluids. When the fluid 14 is either one or the other, it is in fluid contact with the one or more sensors within a sealed housing. When both fluids are present the activating fluid will be referred to as 38 rather than 14. In this case the preconditioning fluid 14 is the controlled-content fluid present outside the sealed housing while the activating fluid 38 is present within the sealed housing. The controlled-content fluid 14 can equilibrate with the one or more sensors that are in an active state in the sensor assembly in order to precondition an active sensor.

The controlled-content fluid can be a gas, liquid or combination of a gas and liquid depending on the state of the analyte that is detected by the sensor. For a nonexclusive example when the analyte is a blood gas such as oxygen and/or carbon dioxide and the controlled-content fluid 14 is a gas one or more of these gases alone or in combination with each other or with inert gases can purge the layer after the sensor assembly 12 is placed in the layer and prior to hermetic sealing. Also it is possible that the controlled-content fluid is Just the inert gas when it may be desired to provide a zero quantity of the analyte in the fluid. When the controlled-content fluid 14 is a combination of gas and a liquid, such a fluid can be produced with the requisite quantity of the gas by any method known to those skilled in the art. For example, such a fluid can be a tonometered fluid produced by any of the commercially available tonometers like the one available from Instrumentation Laboratory under the designation IL237 or by any method known to those skilled in the art like the techniques shown in preparing tonometered buffered solution or whole blood described in the article entitled "Quality Control in Blood pH and Gas Analysis by Use of a Tonometered Bicarbonate Solution and Duplicate Blood Analysis in Clinical Chemistry", Vol. 27 No 10 1981 pages 1761–1763, the description of which is hereby incorporated by reference. For such fluids the liquid can be an aqueous solution that is buffered and contains oxygen and carbon dioxide for use in blood gas measurements. Such solutions can be prepared in accordance with U.S. Pat. No. 3,681,255 the description of which is hereby incorporated by reference.

An example of an equilibrated or tonometered fluid as fluid 14 can result from contact of the buffered liquid solution with the carbon dioxide containing gas which can include a mixture of carbon dioxide with one or more inert gases. An inert gas is one which does not react with the buffer solution to change the pH. This would destroy the predictability of a final pH value. Also, inert gas is one that does not react with any of the ingredients in the preconditioning fluid 14. Nonexclusive examples of inert gases are nitrogen, argon and other similar gases normally found in the air. This includes the noble gases such as neon, argon, krypton, xenon, helium and the like. It is preferred to use as the equilibrating gases for blood gas analysis a mixture of carbon dioxide and nitrogen or carbon dioxide with oxygen and nitrogen. Nonexclusive examples include:
1) around 5 percent carbon dioxide with nitrogen making up the balance of the gas in the fluid and
2) around 7 volume percent carbon dioxide and around 10 volume percent oxygen and the balance is nitrogen and around 1 to around 3 percent carbon dioxide and around 97 to around 99 percent nitrogen.

The controlled-content fluid with the controlled amount of gas or equilibrated with gas is maintained in an environment which prevents the diffusion of gas or vapor into or out of the system to prevent any drifting of the partial pressure values and any change in pH value. Art-recognized apparatus for maintaining this fluid can be used and one such example is the aforementioned commercial tonometer.

In addition, FIG. 2 has a different configuration for the housing and sensor element 15 from that of FIG. 1. Envelope 10 is shown in the form of a bag as in FIG. 1 having the outer layer 34 and inner sealable polymeric layer 36. The sensor element 12 has the nonconducting substrate 16, one or more sensors 18, electrical circuit means 20, and housing 22 with inlet 26, outlet 28 and channel 24 as in FIG. 1. The preconditioning fluid is sealed in the channel 24 and side channels 23 and 25 that connect with channel 24 in the housing 22. When the one or more sensors on the nonconducting substrate are in an active state, the preconditioning fluid can be the controlled-content fluid. One or more of the sensors on the non-conducting substrate 16 may require something other than itself to be active, i.e. the presence of an additional component such as a hydrating fluid. FIG. 2 shows the preferred arrangement of channels and sensors that include sensors 18A, 18B, and 18C and reference electrodes 19A and 19B. The sensors can be for oxygen, carbon dioxide and pH for blood gas analysis. It is also preferred to have the sensor assembly 22 shown in FIG. 2 as the sensor assembly in FIG. 3 for blood gas analysis, and the sensor assembly shown in FIG. 3 is an alternative embodiment.

To provide sealed contact between the activating fluid 38 and the at least one sensor, one part of the channel 24 on each side of the sensor is sealed with the fluid 38 in contact with the sensor. Preferably, this sealing is at the inlet and outlet openings of the channel. The openings 26 and 28 of housing 22 are sealed by a substantially moisture impervious seal 30 and 32, respectively. The opening 26 can serve as an inlet to or outlet from housing 22 that is preferably formed by conical tip 40. Also, the housing 22 at the other end of the sensor assembly 12 from opening 26 can have a flared end 42 encompassing opening 28 that is formed by tip section 44, which preferably has an exterior cylindrical shape and an interior conical shape. The tip 44 is surrounded by flared end 42 which has an inner annular space 46 between the external rim 48 of the flared end 42 and the external surface of tip section 44. The openings 26 and 28 for housing 22 shown in FIGS. 1 and 2 are preferably aligned in the same plane and along the same axis at opposite ends of the channel 24 so channel 24 passes longitudinally through the housing alone the same central axis. This arrangement provides sufficient support of the channel 24 by the housing 22 to receive and/or expel fluid through the channel with pressurized movement. Tip sections 40 and 44 allow for connection or coupling to a device to provide fluid pressure, rapid fluid flow, or suction to cause the fluid, for example, with an analyte to be measured to pass, preferably in non-capillary action or flow, in measuring contact with the one or more sensors 18. The tip section 44 distally located from tip section 40 can be similar to tip section 40 as shown or can be adapted and preferably is adapted to connect with a proximate end of a syringe.

The seals 30 and 32 for the housing 22 to seal the activating fluid 38 in contact with the sensor 18 in FIG. 2 is substantially impervious to liquids and can be, but need not have to be, impervious to gas. Seals 30 and 32 preferably are substantially impervious to air, and they may be comprised of a single layer or multilayer laminate. A suitable single layer material includes metal foil that is capable of sealing by a polymeric material that can be heat-treated or RF (radio frequency) treated for sealing. The multilayer laminate material ordinarily has an interior layer of polymeric material and outside this layer a metal foil layer. A typical laminate can have two or more layers and may have an additional outer polymeric layer to facilitate abrasion resistance or printing on top of the metal foil layer. A non-exclusive example of the metal foil is aluminum. Also the seals can be a material similar to that of the layer 10 as long as the material adheres to the housing and is piercable by at least standard syringe-type needles. Hence, all of the aforementioned materials for layer 10 can also be used for the seals when they meet these criteria.

The seals are puncturable and preferably can and do form a seal that can withstand at least gamma-radiation sterilization. The seals preferably have two sections, an upper section 50 is away from the mouth or openings 26 and 28 of the housing 22 and a lower section 52 is in contact with the tip sections 40 and 42, respectively. The upper section 50 can be an air impervious metal foil, preferably aluminum, and the lower most section 52 can be an adhesive material. Preferably, the seals 30 and 32 are a paper-backed aluminum foil coated with a clear heat sealable coating. The coating can be a blend of a high molecular weight ethylene and vinyl acetate copolymer. A nonexclusive example of a suitable material is an aluminum foil having a heat seal polyester film available under the trade designation "Foilseal 3-6" available from Selig Sealing Products, Inc., 17w745 Butterfield Road, Oakbrook Terrace, Ill. 60181. Such materials generally can have a gas transmission for oxygen that is nil and a water vapor transmission which ranges from around 0.005 to 0.059 GS (grams)/CSI(100in$^2$)/24 hours at 90 percent relative humidity. Such materials provide a seal that when securely attached across the openings 28 and 26 of the channel 10 provide substantial imperviousness to air. These values are obtained on a Permatran-W6 for water transmission and an Ox-tran 1000 for oxygen transmission, and both pieces of equipment are available from Mocon Modern Controls, Inc., 4220 Shingle Creek Parkway, Minneapolis, Minn. 55430.

Alternatively, seals 30 and 32 have the adhesive material 52, which can be thermoplastic resin suitable for hot melt deposition or extrusion lamination. A few nonexclusive suitable examples of these thermoplastic resins include resins known as the so-called hot-melt type adhesive, such as polyethylene, an ethylene/vinyl acetate copolymer (EVA) or a partially saponified EVA. Also, the seals 30 and 32 can be a composite of an aluminum/polypropylene film with a heat sealable resin such as a polyamide, polyolefin, and saturated polyesters. When sealing to adhere the resin to the polymeric surface of the housing and thereby adhere the seal to housing 22, the sealing is performed by heat sealing. Any induction sealing or any heat sealing method known to those skilled in the art can be used. The seals 30 and 32 can have any shape suitable for covering completely openings 26 and 28 and providing for a snug fitting with the flat surface of the tips 40 and 44. Preferably, the seal is in the form of a disc having a diameter similar to the diameter across the tips 40 and 44, respectively.

Generally, in FIG. 2 the activating fluid 38 usually does but may not completely fill the channel of the housing. A nonexclusive example of a suitable process for placing the requisite quantity of analyte-containing 14 or activating fluid 38 in contact with the sensor assembly 12, purging the layer 10 formed into a bag with the requisite composition of fluid, and hermetically sealing the layer bag 10 occurs in the following manner.

One of the openings of the channel 24 is sealed which can be either opening 26 sealed with seal 30 or opening 28 sealed with seal 32 by a heat sealing but preferably an induction sealing process. After the sealing of one end, the preconditioning fluid 14, whether activating or controlled-content fluid, is added to channel 24 and any side channels that may be present to fill substantially all of the channels. Although small amounts of air bubbles can be tolerated in the channels, preferably the channels are filled to capacity. The remaining opening of the housing is sealed with the other seal through a heat sealing process but preferably an induction sealing process. In general, the sealing should overcome the hurdle of adhering the seal to a plastic or polymeric substrate in a possibly moist environment since there may be moisture or liquid on the surface of tips 40 and 44 after the addition of the hydrating fluid. In general, however, satisfactory results are obtained by conducting the heat sealing at a temperature higher than the softening or melting point of the heat sealable resin and the pressure is sufficient if it doesn't cause excessive or substantial flow of heat sealable resin away from the area to be sealed. For heat sealing of a polypropylene heat sealable resin, the seal pressure can be in the range of around 2 to around 5 kilograms per centimeter$^2$ (Kg/cm$^2$) for the temperature of heat sealing in the range of 180° C. to 300° C. For a polyamide, like Nylon 12, heat sealable resin the pressure can be in the range of 2 to 7 Kg/cm$^2$ for the temperature of sealing of around 200° C. to 300° C. For polytetramethylene terephthalate the seal pressure can be around 2 to 7 Kg/cm$^2$ for the sealing temperature in the range of 220° C. to 320° C. The time required for heat sealing varies depending on the thickness of the heat sealable resin layer.

Generally, heat-sealing or RF sealing occurs by applying the heat or RF to the metal foil layer directly or indirectly which radiates the heat to the polymeric layer that is contacting another polymeric layer at the edge of the bag and the heat causes the polymeric layer to diffuse to seal the bag. The heat sealing is conducted for a time sufficient to perform melting and bonding of the sealable resin, for example 0.1 to 5 seconds. The heat sealing operation can be performed in an operation comprised of one stage or two or more stages. In the latter case, the same or different temperature and pressure conditions as those aforementioned can be adopted at these stages. The formed sealed area is cooled, if necessary, under application of pressure by optional means to form a sealed area with good sealing efficiency. For instance, immediately after completion of the heat sealing operation, the heat sealed area in which the resin is still in the softened or molten state is pressed by two positively cooled press bars whereby the resin is solidified. Although any operation known to those skilled in the art to cool and harden the adhesive polymer can be used.

For induction sealing, generally any induction sealing process known to those skilled in the art of induction sealing can be used. A nonexclusive example of a suitable process involves placing the housing 22 with seal 30 or 32 in place over the opening 26 or 28, respectively, of the channel 24 on the flat surface of the rim of one of the tips 40 or 44, respectively. With the seal in place over the opening, that end of the housing with the seal over the opening is held with the application of pressure against a region where it is exposed to high-frequency electromagnetic waves. A suitable piece of equipment is that available from Giltron, Inc., Medfield, Mass. 02052, referred to as Foil Sealer Induction Heat Sealer, Model PM1. The aluminum foil of the seal is locally heated to a point whereby it heats and melts the adjacent resin layer. The melted resin layer adheres to the top horizontal surface of the rim of the tip that surrounds the opening. The hydrating fluid is placed in the channel in the aforementioned manner and the other seal is placed over the other opening at the other tip and subjected to induction heating in the same manner to seal the other end.

Also the method of sealing depends to a degree on the presence of any securing means used to maintain the seals 30 and 32 in a snug relationship to the tips 40 and 44, respectively. The seals 30 and 32 can have any shape suitable for covering completely openings 26 and 28 and providing for a snug fitting with the flat surface of the rims of the tips 40 and 44.

The sensor assembly 12 with the sealed activating fluid 38 in fluid contact with the one or more sensors 18 is placed in the layer bag 10 and the last unsealed edge or all of the edges are sealed at this time. The manner of sealing can be the heat or induction sealing methods as aforementioned for the seals to the housing except with the use of a different attachment to fit over the edges to make the seal.

FIG. 3 discloses the preferred embodiment of the present invention where in addition to the presence of the sensor assembly in the layered envelope 10 there is also present a sample collection means 54 and a calibrant delivery means 56. Most preferably, these means are affiliated with the sensor assembly 12 in a user friendly fashion. Also it is preferred to have two preconditioning fluids present in the bag. One fluid is a controlled-content fluid and the other is an activating fluid since in the preferred embodiment at least one sensor is present that has at least one hydratable membrane.

In the bag or envelope of FIG. 3, the sensor assembly 12 is shown fixedly attached to sample collection device 54, hereinafter referred to as the "collector", and received in a calibration device 56, hereinafter referred to as the "calibrator". Preferably the sensor assembly 12 is that of FIG. 2 fixedly attached at one end to a collector that is a syringe and to the other end slideably received in the calibrator so that, respectively, seals 30 and 32 remain intact in the envelope 10.

The collector of the collector 54 has a first fluid communicating chamber 58 and the sensor assembly 12 has channel 24 as a second fluid communicating chamber that other than for a fluid seal 32 communicates with the first fluid communicating chamber. The body portion of the collector 54 may be made from a suitable plastic material such as a suitable clear styrene plastic.

The first chamber 58 defines a cylinder 60 with a piston 62 slidable therein. The piston is resilient and may be made of plastic, rubbery or elastomeric material, as for example clear polystyrene or polycarbonate. The piston 62 and the cylinder 60 are circular in cross section and the piston 62 is seated on a seat 64 provided at one end of the first chamber 58 nearest the second chamber. The piston 62 is provided with a centrally disposed, axially extending aperture 66 that has an expanded diameter after an initial narrower diameter to form lip 68.

The piston 62 is actuated by an actuating means 70 which includes a reciprocal actuator 72 mounted for reciprocal movement within collector 54 which is preferably a syringe. This movement can be initiated manually by application of force on annular member 74 projecting outwardly from the proximate end of the reciprocal actuator 72. This is the case were the actuator 72 is a typical plunger of a typical syringe and where the actuator is associated with spring 76 in a spring biased sleeve 78. The sleeve 78, which may be made of polystyrene, is slidably mounted on the syringe body portion of collector 54.

The spring 76, which may be in the form of a stainless steel helical spring, is disposed in an annular groove 80 in the sleeve 78 and provides a biasing force counter to the slidable movement of the sleeve 78 and its associated actuator toward the piston 62.

The reciprocal actuator 72, which may be a solid or hollow member defining a cavity 82 therein, is provided with a first shaft portion 84 terminating at one end in a raised portion 86 and at the other end in the skirt portion 88 of a first puncturing means in the form of a puncturing head 90, formed on the end thereof. The reciprocal actuator 72 is further provided with a second shaft portion 92 terminating at one end in a generally planar, annular member 74 and at the other end in the raised portion 86.

As best seen in FIG. 3, the biasing force of the spring maintains a clearance between the seal 32 of the sensor assembly 12 and the puncturing head 90 of the reciprocal actuator 72 when the collector/syringe 54 and calibrator 56 are in layer envelope 10. Further, the reciprocal actuator 72 is provided with an annular rib 74 which extends about the end of the sleeve 78 and maintains the position of the reciprocal actuator 72 with respect to the spring biased sleeve 78 until overridden by grasping the annular member 74 and moving the reciprocal actuator 72 out from the sleeve 78. The spring biased sleeve 78 is guided, for movement with respect to the syringe body portion 58, by resilient fingers 96 (not shown) which are received in longitudinally extending slots (not shown) provided in wall of the syringe body portion 58.

The piston 62 is slidably restrained on the shaft portion 84, by and between the skirt portion 88 and the raised portion 86, for lost motion between the piston 62 and the reciprocal actuator 72, whereby the piston 62 will remain stationary on the shaft portion 84 when not engaged by the skirt portion 88 or the raised portion 86.

The sensor assembly 12 as in FIG. 2 has channel 24 the outlet 28 of which is engaged with an inlet 68 of the collector 54 for fluid communication. Seals 30 and 32 maintain the activating fluid 38 in fluid contact with the one or more and preferably three sensors 18. Preferably the three sensors are thick film sensors having hydratable polymeric membranes. In this case the activating fluid preferably is a hydrating fluid which is chiefly an aqueous fluid with an effective composition to hydrate at least to a partial degree but better to a substantial degree the hydrophilic polymeric membranes. The hydrating fluid 14 is any liquid suitable for maintaining the membrane of sensor 18 in a non-dried state. For instance, the liquid will have some amount of water although a minor quantity of organic liquids may also be present. Preferably, the liquid is a stable liquid for storage ranging from a short time (days or weeks) to prolonged periods of time of several months to one or two years. Preferably, the liquid is an aqueous solution that is isotonic with any electrolyte in the one or more sensors. More preferably, the activating fluid 38 as a hydrating fluid in a sealed sensor assembly is also isotonic to act as the electrolyte for any reference electrodes that may be present in the sensor assembly 12 as reference electrode 18A as shown in FIG. 3 or as 19(a) and/or 19(b) as shown in FIG. 2. A suitable example of a hydrating fluid for the measurement or detection of blood gases is an aqueous solution of salts. A suitable example of a hydrating fluid is an aqueous solution comprising: disodium hydrogen phosphate, potassium dihydrogen phosphate, sodium bicarbonate, and sodium chloride. Such a solution can have a varying range of amounts for the individual constituents but most preferably for the aforelisted salts the amounts are in millimoles per kilogram of water in the order listed as follows: 4.8, 13, 22, and 12.5. Another nonexclusive example is an aqueous solution of around 100 millimoles of sodium chloride with or without buffers. The quantity of hydrating fluid in channel 24 or any plurality of channels is at least that which is sufficient to cover or remain in contact with the one or more sensors. For example, seals 30 and 32 of FIG. 2 could be in channel 24 rather that at the opening so as to maintain the hydrating fluid 14 in contact with the one or more sensors. In this situation the seals 30 and 32 would be more plugs rather than foil-backed seals.

The sensor assembly 12 and the collector 54 may be integrally formed with the syringe body portion of the collector 54 or may be fixedly attached to the collector 54 by means of interlocking fingers (not shown) provided on the collector 54 which engage a complementary groove provided on the interior surface of the cup-like end of the sensor assembly 12.

The sensing assembly 12 may be in the form of an electrode assembly and may be provided with a suitable connecting cable 102 which would have suitable electronic connection fitting for connecting the sensor assembly 12 to a signal processing means (not shown) to process the output signal of the sensor assembly 12. The sensor assembly 12 preferably employs miniature thick film electrodes or microsensors 18 and 18A for measuring analytes, e.g., pH, pO2 and pCO2 in fluids, and in particular blood. Such miniature electrodes or microsensors for measuring analytes are known and described in U.S. Pat. Nos. 4,339,317 and 4,615,340.

The calibrator 56 is provided for calibrating the sensor assembly 12 through inlet 26 of the sensor assembly to insure that the measurement of the analytes is accurate. Basically, the calibration of the sensor assembly 12 involves contacting the microsensors of the sensor assembly 12 with a solution of a predetermined analyte concentration preferably pH, pO2 and pCO2 values for measuring blood gases. With this contact the microsensor outputs are measured and calibration coefficients are calculated using software algorithms, all of which is conventional and known in the art, for example, as described in U.S. Pat. No. 4,734,184.

The calibrator 56 includes a body portion defining a cylinder 104 open at one end for receiving at least a portion of the collector 54. A movable member 106, carrying a second seal puncturing means, which may be in the form of a double ended, hollow, stainless steel needle 108, is slidably received in the cylinder 104. The movable member 106 is provided at least one resilient finger 110 which resiliently engage slots provided in the wall of the calibrator 56 to positionally hold the movable member 106 at the start and end point of its travel within the calibrator 56. The travel of the movable member 106 within the cylinder 104 is limited by inwardly facing projections 112 formed on the interior surface of the cylinder 104.

A sealed container 114 containing calibration solution 116, with the above mentioned characteristics, is supported in the end of the cylinder 56 of the calibrator 54, opposite the opening receiving the sensor assembly 12. The mouth of the container 114, is sealed by a puncturable cap 118 Suitable containers depending on the type of calibration fluid include glass vials with an elastomeric stopper or with an induction seal with a snap-cap and plastic containers with similar or different caps or stoppers. If a plastic container is employed, it should be coated with a suitable barrier coating to essentially eliminate any O2 or CO2 permeability of the plastic container to retain the integrity of the calibration solution.

The container 114 is seated and centrally received in a cup member 120, the cup member 120 being centrally aligned in the calibrator 56 by any device known to those skilled in the art for instance by a plurality of inwardly facing projections formed on the interior surface of the cylinder 104. The cup member 120 may be made from a suitable plastic material and is sealingly received by the calibrator 56 at cylinder 104.

The calibrator 56 and the sensor assembly 12 and the collector 54 can be held together as a unit in the hermetically sealed envelope 10 or can be present in the envelope as separate devices. In the former case any clip or pin or clamp known by those skilled in the art for holding two columnar articles together can be used. For example a suitable clamp is a substantially C-shaped clamp which clampingly engages at least portion of the exterior surface of the calibrator 56 (not shown in FIG. 3). Preferably the longitudinal axis of the calibrator 56 is coincident with the longitudinal axis of the collector 54.

Preferably, a conical shape of tips 40 and 44 is of a standard outer diameter to allow for connection to sample gathering means such as needles or tubing or conduit from catheters or tubing in multi-sequential analyzing equipment. Most preferably, the conical shape is suitable for a Leur-Lok fitting or attachment to a sample gathering means not shown in FIG. 3 such as a needle for a syringe.

After the sensor assembly 12, collector 54 and calibrator 56 are placed in the layer envelope 10, the envelope is purged with the second preconditioning fluid which is the controlled-content fluid 14. The controlled-content fluid is similar to that described for FIG. 2. With this addition the envelope is sealed by heat or induction sealing at the last remaining edge so that the previously sealed edges of the layer 10 provide an envelope or bag to hold the controlled-content fluid 14. The sealing is accomplished in a manner similar to the envelopes for FIGS. 1 and 2.

Generally, the heat sealing is conducted for a time sufficient to perform melting and bonding of the sealable resin, for example 0.1 to 5 seconds. The heat sealing operation can be performed in an operation comprised of one stage or two or more stages. In the latter case, the same or different temperature and pressure conditions as those aforementioned can be adopted at these stages. The formed sealed area is cooled, if necessary, under application of pressure by optional means to form a sealed area with good sealing efficiency. For instance, immediately after completion of the heat sealing operation, the heat sealed area in which the resin is still in the softened or molten state is pressed by two positively cooled press bars whereby the resin is solidified. Although any operation known to those skilled in the art to cool and harden the adhesive polymer can be used.

When the hermetically sealed sensor apparatus of the present invention needs to be sterilized, the hermetically sealed sensor can be sterilized by gamma-sterilization or pasteurization sterilization. For example the hermetically sealed sensor apparatus as depicted in FIGS. 1–3 can be sterilized as an entire unit. A nonexclusive example of a pasteurization technique that can be used with the hermetically sealed sensor apparatus of the present invention is heating one or more of them at a temperature of around 70° C. for eight hours. The gamma-radiation sterilization can occur with the use of any gamma-sterilization equipment known to those skilled in the art. For pasteurization sterilization, the cooling rate should be such that in the total heat history given the channels is accomplished over an adequate period of time.

When the hermetically sealed sensor apparatus with all of its contents undergo sterilization by gamma-radiation, initial oxygen concentrations can be altered for certain types of fluid compositions. The gas composition of the controlled-content fluid 14 in FIGS. 2 or 3 preferably contains little if any oxygen but some oxygen may be present in fluid 14 when gamma-sterilization is used. Gamma-sterilization consumes oxygen thereby reducing any oxygen initially present in fluid 14 or equilibrated into fluid 38.

Figure 4:
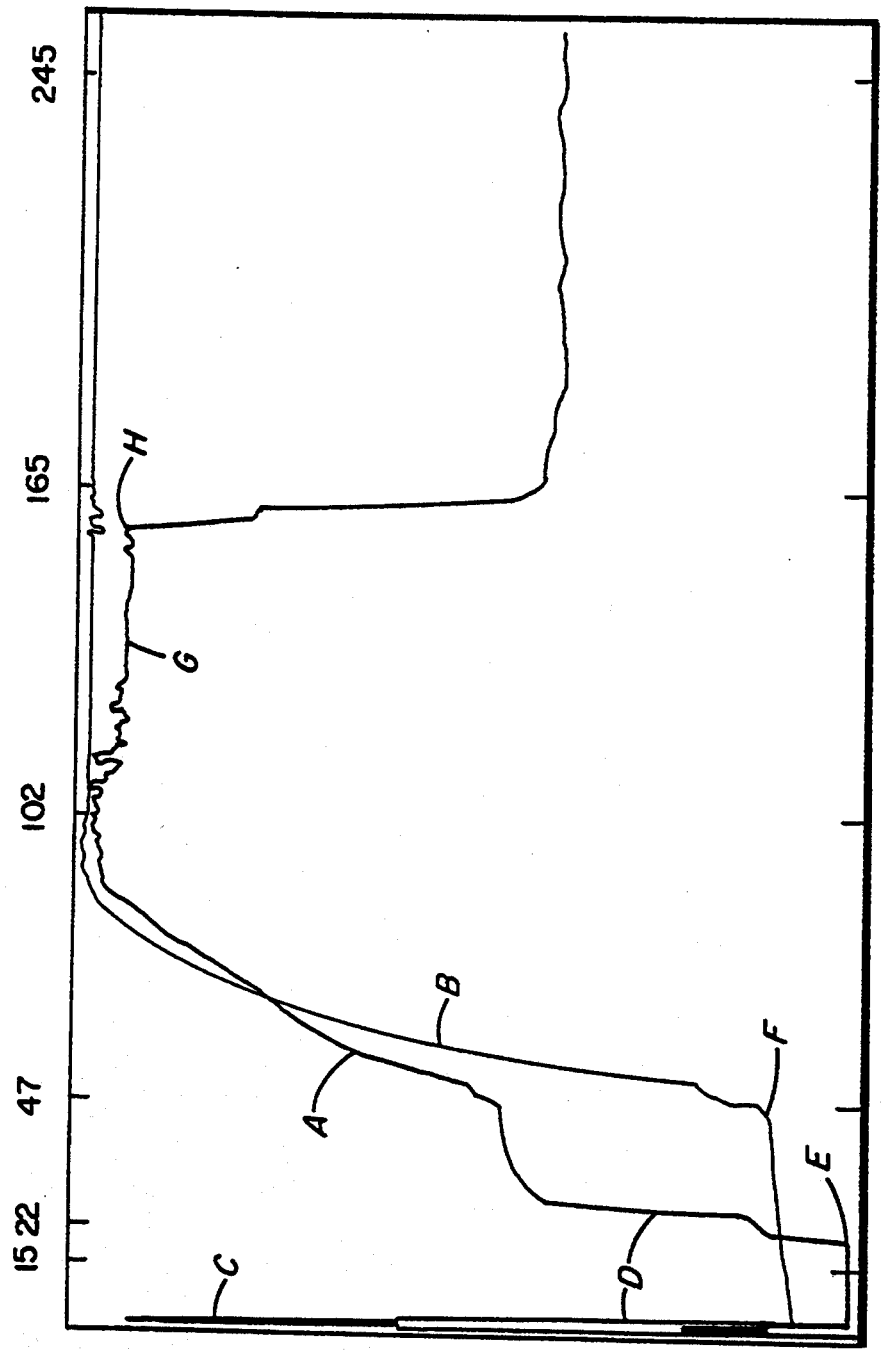
FIG. 4 is a graph of nanoamps along the ordinate and seconds along the abscissa showing the performance of the activated sensor device of the present invention.

FIG. 4 shows a graph of the nanoamp output of the sensor over time for the sensor in the sensor-collector-calibrator apparatus of the sensor apparatus of the present invention as shown in FIG. 3, where the two preconditioning fluids are present. One fluid is the controlled-content fluid and the other is the activating fluid that is the hydrating fluid. A third fluid is present in the calibrator and it is the calibration fluid. The known-content fluid 14B can have a composition of around 5 percent carbon dioxide with nitrogen making up the balance of the gas in the fluid. The calibration fluid had known values of carbon dioxide and oxygen such as around 7 volume percent carbon dioxide and around 10 volume percent oxygen with the balance as nitrogen. The sensors in the sensor assembly included an oxygens carbon dioxide and pH sensor with accompanying reference electrodes in the case of carbon dioxide and pH much like that shown in FIG. 2. Nanoamps are along the ordinate while the time is along the abscissa.

Curve A is the nanoamp output and Curve B is the temperature of a heater present on the nonconducting substrate along with at least the oxygen sensor. The peak at C is when the cable 102 is plugged into a measuring device. The time period indicated as D is the time period that the equilibrated hydrating fluid which is the activating fluid in the sensor assembly 12 is read by the measuring instrument. Here, both the controlled-content fluid and the activating fluid are essentially devoid of and preferably do not contain any oxygen. The calibrant is introduced across the sensor at point E and the oxygen sensor begins to read the oxygen concentration in the calibration fluid 116 of FIG. 3. The current output of the oxygen sensor tracks the oxygen until the heater clicks in at point F and heats the calibration fluid to a temperature similar to the temperature at which the unknown sample has when collected. For example, blood when collected has a body temperature of around 98.6° F. The current output from the sensor measuring the oxygen concentration of the calibration fluid stabilizes in about 30 seconds to give a value of the oxygen concentration at the desired temperature for the calibration fluid as indicated at range G in the curve. At point H the blood sample is introduced and the current output of the sensor in this case decreases to measure the oxygen concentration of the blood gas sample.

When the calibration fluid is introduced, the electronic measuring means detects both the carbon dioxide and the pH of the calibrant because the carbon dioxide equilibration with the known-content fluid can cause a change in the pH. The concentration of the carbon dioxide and the pH of the equilibrated hydrating fluid are known as is that for the calibrant in the vial 116 since the calibrant in the vial is not equilibrated with the known-content fluid 14B. There is no equilibration since the vial is hermetically sealed from the atmosphere in layer 10. When the calibrant is introduced at point E of the chart, the current signal changes by some known amount and this change is compared to a statistical average of changes occurring for numerous samples to ascertain if the change meets the minimum criteria for sensor operability. This tests the sensitivity of the sensor to determine if it is accurate. For utilizing a 1 point calibration in determining concentration values of samples, the determination and sensitivity of the sensor is important even in calibrating for the offset of the sensor from the origin of a relationship of current output over time as indicated in FIG. 4.

In this way the hydrating fluid that is equilibrated with the controlled-content fluid is used as a diagnostic check for adequate operability of the sensor. This is important in the use of portable sensors as a check for whether or not the sensor is properly operating.

In the situation of the sensor including an oxygen sensor, a carbon dioxide sensor and a pH sensor and two reference electrodes for the carbon dioxide sensor and pH sensor, a 1 point calibration can be performed. For a 1 point calibration, the slope of the line or the offset from the origin must be known. In order to determine the offset of the oxygen sensor, the sensor current in the absence of oxygen must be known . Therefore, the envelope layer 10 and its packaged sensor assembly with the preconditioning fluids are arranged so that the controlled-content fluid is free of oxygen or contains very little oxygen that may be consumed during gamma-sterilization and this controlled-content fluid is allowed to equilibrate across the housing material of the sensor assembly with the second preconditioning fluid that is the hydrating or activating fluid. After the unit is plugged into the measuring module, the unit looks at the current of the oxygen sensor. If no oxygen is present, the current is read by the unit as the offset. So the amount of current read when current is first plugged in indicates if the sensor is good or not. A standard is set for background current and the sensor unit is checked to see if the oxygen sensor meets the offset requirements of zero or essential zero.

The preconditioning fluid with the controlled-content fluid in the pouch layer 10 allows the test for the offset limit without the need of using difficult solutions such as sulfides and the like to determine the offset of the oxygen sensor. The offset for the oxygen concentration is measured before the calibrating fluid is in contact with the oxygen sensor and before heating, since the oxygen sensor has a temperature coefficient. With the known carbon dioxide value in the controlled-content fluid, the carbon dioxide and pH sensor can be calibrated. Both of these sensors have a certain sensitivity in millivolts per millimeters of mercury for carbon dioxide tension. This is determined via a statistical process by measuring many samples which are compared against the sensor being checked. The monitor means checks or predicts the millivolt change from the millivolts measured for the hydrating fluid and the calibrant fluid and this change should be within the statistical range of acceptable values or the sensitivity of the sensor is not within specifications.

The calibrant is introduced over the sensor when the sensor assembly with collection means and calibrating means is removed from the hermetically sealed envelope or layer 10. After removal, the unit is appropriately assembled and the calibrant is introduced over the sensor. In the time it takes to remove the sensor from the hermetically sealed envelope and to introduce the calibrant, the unit was already plugged into the measuring module and the module was measuring the analytes carbon dioxide and the pH preferably in the preconditioning fluid that is the equilibrated hydrating fluid.

We claim:

1. A preconditioned sensor apparatus, comprising:
    sensor assembly having a housing that has at least one opening for receipt of fluids and that has one or more sensors in an activated state for detecting one or more analytes where the sensors are present in the housing for fluid contact with the opening and where the sensors communicate with an electrical circuit means for transmission of signals from the sensors,
    a hermetically-sealed envelope of gas impermeable material selected from the group consisting of; single layer or multiple layer laminate to enclose the sensor assembly, and
    at least one preconditioning fluid present in between the sensor assembly and the envelope selected from the group consisting of an activating fluid for fluid contact with the one or more sensors, and controlled-content fluid within the envelope for contact with the sensor assembly, wherein the controlled-content fluid has inert fluid or known amount of one or more analytes that are measured by the one or more sensors with or without the presence of inert fluid.

2. Apparatus of claim 1 wherein the controlled-content fluid is selected from the group consisting of: gas, liquid, combinations of a gas and liquid; moist air; air with a relative humidity greater than around 30 percent, super-saturated moist air, moisture-containing inert gas, oxygen, carbon dioxide, and mixtures thereof and mixtures with inert gases; tonometered combinations of gas and liquids; and tonometered buffered solution.

3. Apparatus of claim 2 wherein the controlled-content-fluid is selected from the group consisting of: mixtures of carbon dioxide and nitrogen, and carbon dioxide with oxygen and nitrogen, including:
1) around 5 percent carbon dioxide with nitrogen making up the balance of the gas in the fluid, and
2) around 7 volume percent carbon dioxide and around 10 volume percent oxygen and the balance is nitrogen
all of which are useful as equilibrating gases for blood gas analysis.

4. Apparatus of claim 2 wherein the inert gases are selected from the group consisting of: nitrogen, argon and other inert gases normally found in the air, and the noble gases.

5. Apparatus of claim 2, wherein the preconditioning fluid is selected from the group consisting of: moist air, air with a relative humidity greater than around 30 percent, super-saturated moist air, moisture-containing inert gas is present in the envelop from the sealed presence of the fluid in the within the hermetically sealed envelope.

6. Apparatus of claim 1 wherein the sensor assembly includes a housing that has at least a portion that is analyte permeable over a period of time and that encompasses the sensor assembly, wherein the housing has a activating fluid in sealed contact with the one or more sensors to assist in maintaining the sensor in an activated condition.

7. Apparatus of claim 1 wherein the sensor assembly has a housing that is permeable over a period of time to one or more analytes of the controlled-content fluid and wherein the housing also has the controlled-content fluid in contact with the one or more sensors.

8. Apparatus of claim 1 wherein the sensor assembly has a housing that is permeable over a period of time to one or more analytes of the controlled-content fluid and wherein the housing has a sealed activating fluid in contact with the one or more sensors and also has the one or more analytes of the controlled-content fluid in contact with the sensor through the housing for equilibration so that the one or more sensors that are in an active state are preconditioned active sensors.

9. Apparatus of claim 1 wherein in addition to the sensor the apparatus has a sample delivery means within the envelope.

10. Apparatus of claim 1 wherein in addition to the sensor the apparatus has a calibrant delivery means within the envelope.

11. Apparatus of claim 1 wherein the housing of the sensor assembly has a channel extending from the opening and the housing has a second opening for the channel that is spaced apart from the first opening so that the channel is positioned for sample interface with the one or more sensors between the openings.

12. Apparatus of claim 11 wherein the housing has the channel with two seals one at each end of the sensor location in the channel, and the housing includes activating fluid in the channel between the seals so that the activating fluid is in sealed contact with the one or more sensors.

13. Apparatus of claim 12 wherein the housing has the channel with two seals where one is in sealing contact with each opening of the housing.

14. Apparatus of claim 11 wherein the seals are selected from the group consisting of: heat sealing seals, radio frequency sealing seals and induction sealing seals.

15. Apparatus of claim 11 wherein the seals are multiple layered seals that are gas impervious.

16. Apparatus of claim 1 wherein the hermetically-sealed envelope is multiple-layered with an outer layer selected from metal foil polymer laminate materials that are heat-sealed or RF (radio frequency) sealed to form the envelope consisting of: metal foil layer of aluminum and with an interior heat sealable polymeric layer selected from polyethylene, polypropylene, polyvinylidene chloride, nylon, high-density polyethylene, polyester, low permeable thermoplast including polyacrylonitrile-copolymer, polyvinylfluoride, polyvinyl chloride, copolymer of a high proportion of acrylonitrile about 72 percent by weight and a low portion of other monomers, that is thermoelastically workable up to a temperature of about 150° C., a laminate consisting of non-stretch polypropylene and biaxially stretched polypropylene and a laminate consisting of an inner layer of non-stretch polypropylene and nylon as an intermediate layer and biaxially stretched polypropylene as an outer layer.

17. Apparatus of claim 16 wherein the envelope has an outer material selected from the group consisting of: polyvinyl alcohol, biaxially stretched polypropylene, polyester, biaxially stretched nylon and polyvinylidene chloride film, nylon, polyester, polyethylene, and polypropylene.

18. Apparatus of claim 1 wherein the apparatus includes a gas impervious container of calibrant within the hermetically-sealed layer where the calibrant is useful for introduction over the sensors when the layer is opened.

19. Apparatus of claim 1 wherein the housing has a sensor element having the one or more sensors and electric circuit means on a nonconducting substrate wherein the electric circuit means communicates with the one or more sensors by layered or patterned paths to the sensors on either side of the nonconducting substrate, but when on the other side of the substrate from the one or more sensors the paths extend through the substrate in appropriately drilled holes and where the one or more sensors and the electrical circuit means can be selected from thick film, thin film, plating, pressurized laminating and photolithographic etching potentiometric and amperometric sensors and electrical circuit means.

20. A preconditioned sensor apparatus, comprising:
an outer hermetically sealed envelope, wherein the envelope is impervious to gas and moisture and is diffusion-tight,
an atmosphere within the sealed envelope having a controlled amount of oxygen in an amount from 0 to 100 percent,
a sensor assembly in the envelope wherein the assembly has: a housing that is substantially pervious to gas within the envelope over a period of time and that has at least one opening for receipt of fluids, at least one electrochemical sensor present in the housing for fluid contact with the opening, and activating fluid sealed within the housing and in contact with the one or more sensors, wherein the sensor assembly is in contact with the atmosphere for a period of time for equilibrium to be established between the atmosphere within the envelope and the activating fluid in the housing.

21. Apparatus of claim 20 wherein the one or more sensors are blood gas sensors and have at least one hydrophilic membrane in fluid contact with the activating fluid that is a hydrating fluid.

22. Apparatus of claim 21, wherein the blood gas sensors are for measuring the amount of oxygen, carbon dioxide, and the pH of bodily fluids.

23. Apparatus of claim 20 wherein the controlled atmosphere is selected from the group consisting of: mixtures of carbon dioxide and nitrogen, and carbon dioxide with oxygen and nitrogen, including
1) around 5 percent carbon dioxide with nitrogen making up the balance of the gas in the fluid, and
2) around 7 volume percent carbon dioxide and around 10 volume percent oxygen and the balance is nitrogen, around 1 to around 3 percent carbon dioxide and around 97 to around 99 percent nitrogen all of which are useful as equilibrating gases for blood gas analysis.

24. Apparatus of claim 20 wherein the activating fluid is selected from the group consisting of: gas when the electrochemical sensor is other than a thick film sensor; liquid, combinations of a gas and liquid; moist air; oxygen, carbon dioxide, and mixtures thereof and mixtures with inert gases; tonometered combinations of gas and liquids; and tonometered buffered solution.

25. Apparatus of claim 20 wherein the envelope has at least one layer that is selected from the group consisting of: at least one layer that is aluminum foil that is used with a heat sealing polymer and the layer is formed by heat sealing; multiple-layers that are from metal foil polymer laminate materials that are heat-sealed or RF (radio frequency) sealed to form the envelope consisting of: metal foil layer of aluminum and an interior heat sealable polymeric layer selected from polyethylene, polypropylene, polyvinylidene chloride, nylon, high-density polyethylene, polyester, low permeable thermoplast including polyacrylonitrile-copolymer, polyvinylfluoride, polyvinyl chloride, copolymer of a high proportion of acrylonitrile about 72 percent by weight and a low portion of other monomers, that is thermoelastically workable up to a temperature of about 150° C., a laminate consisting of non-stretch polypropylene and biaxially stretched polypropylene and a laminate consisting of an inner layer of non-stretch polypropylene and nylon as an intermediate layer and biaxially stretched polypropylene as an outer layer.

26. Apparatus of claim 20 wherein the time element is at least around 24 hours.

27. A preconditioned sensor apparatus, comprising:
an outer hermetically sealed envelope, wherein the envelope is impervious to gas and moisture and is diffusion-tight and is at least a bilayered material with an outer layer of aluminum and an inner layer of a heat sealing polymeric material;
an atmosphere within the sealed bag selected from the group consisting of: mixtures of carbon dioxide and nitrogen, and carbon dioxide with oxygen and nitrogen, including
1) around 5 percent carbon dioxide with nitrogen making up the balance of the gas in the fluid, and
2) around 7 volume percent carbon dioxide and around 10 volume percent oxygen and the balance is nitrogen, carbon dioxide from around 1 to around 3 percent and the balance nitrogen, all of which are useful as equilibrating gases for blood gas analysis;
a sensor assembly in the envelope wherein the assembly has:
a housing that has;
i) a portion that is pervious to gas within the envelope over a period of time,
ii) at least one opening for receipt of fluids,
at least one electrochemical sensor having at least one hydratable membrane and present in the housing for fluid contact with the opening, and
hydrating fluid sealed in contact with the one or more sensors, wherein the sensor assembly is in contact with the atmosphere for a period of time for equilibrium to be established between the atmosphere within the envelope and the hydrating fluid in the housing.

28. A preconditioned sensor apparatus, comprising:
an outer hermetically sealed envelope, wherein the envelope is impervious to gas and moisture and is diffusion-tight and is at least a bilayered material with an outer layer of Aluminum and an inner layer of a heat sealing polymeric material;
an atmosphere within the sealed envelope selected from the group consisting of: mixtures of carbon dioxide and nitrogen, and carbon dioxide with oxygen and nitrogen, including 1) around 5 percent carbon dioxide with nitrogen making up the balance of the gas in the fluid, and
2) around 7 volume percent carbon dioxide and around 10 volume percent oxygen and the balance is nitrogen, carbon dioxide from around 1 to around 3 percent and the balance nitrogen, all of which are useful as equilibrating gases for blood gas analysis;

a sensor assembly in the envelope wherein the assembly has:
 a) a housing that has;
  a portion that is pervious to gas within the envelope over a period of time,
  at least one opening for receipt of fluids, and
  a channel extending from the opening and wherein the housing has a second opening for the channel that is spaced apart from the first opening and wherein the channel has two seals one at each end of the sensor location in the channel,
 b) at least one electrochemical sensor having at least one hydratable membrane that is present in the housing for fluid contact with the channel, and
 c) hydrating fluid between the seals in sealed contact with the one or more sensors, and wherein the sensor assembly is in contact with the atmosphere for a period of time for equilibrium to be established between the atmosphere within the envelope and the hydrating fluid in the housing;

calibrating means having a hermetically sealed calibrant solution having known amounts of the one or more analytes to be measured by the one or more sensors and adapted for engagement with the sensor assembly; and sample collecting means adapted for engagement with the sensor assembly.

29. Apparatus of claim 28, wherein the sensor apparatus is sterilizable.

30. A preconditioned sensor apparatus, comprising:
a sensor element having
 a) a housing that has;
  i) a portion that is pervious to one or more gases over a period of time,
  ii) at least one opening for receipt of fluids,
  iii) a channel extending from the opening, wherein the channel has a second opening that is spaced apart from the first opening, and where the channel has two puncturable, multiple layered, and gas impervious seals wherein the seals are selected from the group consisting of: heating sealing seals, radio frequency sealing seals and induction sealing seals,
 b) at least one electrochemical sensor having at least one hydratable membrane which is present in the housing for fluid contact with the channel and between the two seals,
 c) and hydrating fluid between the seals in sealed contact with the one or more sensors;

a fluid impermeable, diffusion-tight, envelope hermetically sealed to enclose the sensor assembly and, wherein the hermetically-sealed envelope is multiple-layered and selected from metal foil polymer laminate materials that are heat-sealed or RF (radio frequency) sealed to form the envelope, wherein the laminate consists of: metal foil layer of aluminum and an interior heat sealable polymeric layer selected from polyethylene, polypropylene, polyvinylidene chloride, nylon, high-density polyethylene, polyester, low permeable thermoplast including polyacrylonitrile-copolymer, polyvinylfluoride, polyvinyl chloride, copolymer of a high proportion of acrylonitrile about 72 percent by weight and a low portion of other monomers, that is thermoelastically workable up to a temperature of about 150° C., a laminate consisting of non-stretch polypropylene and biaxially stretched polypropylene and a laminate consisting of an inner layer of non-stretch polypropylene and nylon as an intermediate layer and biaxially stretched polypropylene as an outer layer; and a preconditioning fluid selected from the group consisting of: mixtures of carbon dioxide and nitrogen, and carbon dioxide with oxygen and nitrogen, including
1) around 5 percent carbon dioxide with nitrogen making up the balance of the gas in the fluid, and
2) around 7 volume percent carbon dioxide and around 10 volume percent oxygen and the balance is nitrogen, carbon dioxide from around 1 to around 3 percent and the balance nitrogen, where the preconditioning fluid is present within the envelope for a period of time to establish equilibrium with the hydrating fluid in the sensor element.

31. A preconditioned sensor apparatus, comprising:
sensor assembly having a housing that has at least one opening for receipt of fluids and that has sensors for measuring the amount of oxygen, carbon dioxide, and the pH of bodily fluids, where the sensors are in an activated state while present in the housing for fluid contact with the opening and where the sensors communicate with an electrical circuit means for transmission of signals from the sensors, a hermetically-sealed envelope of gas impermeable material selected from the group consisting of: single layer or multiple layer laminate to enclose the sensor assembly, and at least one preconditioning fluid present in between the sensor assembly and the envelope selected from the group consisting of an activating fluid for fluid contact with the one or more sensors, and controlled-content fluid within the envelope for contact with the sensor assembly, wherein the controlled-content fluid has inert fluid or known amount of one or more analytes that are measured by the one or more sensors with or without the presence of inert fluid.

* * * * *

UNITED STATES PATENT AND TRADEMARK OFFICE
CERTIFICATE OF CORRECTION

PATENT NO. : 5,421,981

DATED : June 6, 1995

INVENTOR(S) : Leader et al.

It is certified that error appears in the above-identified patent and that said Letters Patent is hereby corrected as shown below:

Claim 1, colum 17, line 29, delete ";" and insert ":"
Claim 5, column 17, line 65, delete "," after the word "air" and insert --;--
Claim 14, column 18, line 45, delete "claim 11" and insert --claim 12--
Claim 15, column 18, line 48, delete "claim 11" and insert --12--
Claim 27, column 20, line 46, delete ";" and insert --:--
Claim 28, column 21, line 11, delete ";" and insert ":"
Claim 30, column 21, line 43, delete ";" and insert ":"
Claim 30, column 21, line 53, delete "heating" and insert --heat--

Signed and Sealed this

Sixth Day of October, 1998

Attest:

BRUCE LEHMAN

Attesting Officer      Commissioner of Patents and Trademarks